United States Patent
Lehr

(10) Patent No.: US 10,392,514 B2
(45) Date of Patent: Aug. 27, 2019

(54) STORAGE-STABLE DYE SOLUTIONS

(71) Applicant: Archroma IP GmbH, Reinach (CH)

(72) Inventor: Friedrich Lehr, Efringen-Kirchen (DE)

(73) Assignee: Archroma IP GmbH, Reinach (CH)

( * ) Notice: Subject to any disclaimer, the term of this patent is extended or adjusted under 35 U.S.C. 154(b) by 0 days.

(21) Appl. No.: 15/124,813

(22) PCT Filed: Mar. 27, 2015

(86) PCT No.: PCT/EP2015/000662
§ 371 (c)(1),
(2) Date: Sep. 9, 2016

(87) PCT Pub. No.: WO2015/144315
PCT Pub. Date: Oct. 1, 2015

(65) Prior Publication Data
US 2017/0022366 A1 Jan. 26, 2017

(30) Foreign Application Priority Data

Mar. 28, 2014 (EP) .................................. 14001158
May 27, 2014 (EP) .................................. 14001844

(51) Int. Cl.

| | | |
|---|---|---|
| *C09B 69/04* | (2006.01) | |
| *C09B 29/00* | (2006.01) | |
| *C09B 29/33* | (2006.01) | |
| *C09B 29/36* | (2006.01) | |
| *C09D 11/328* | (2014.01) | |
| *C09B 67/00* | (2006.01) | |
| *C07C 215/08* | (2006.01) | |
| *C07C 215/12* | (2006.01) | |
| *C09B 29/01* | (2006.01) | |
| *C09B 29/42* | (2006.01) | |
| *C09B 67/44* | (2006.01) | |
| *C09B 29/52* | (2006.01) | |

(52) U.S. Cl.
CPC .......... *C09B 69/045* (2013.01); *C07C 215/08* (2013.01); *C07C 215/12* (2013.01); *C09B 29/0011* (2013.01); *C09B 29/338* (2013.01); *C09B 29/3626* (2013.01); *C09B 29/3669* (2013.01); *C09B 67/0083* (2013.01); *C09D 11/328* (2013.01)

(58) Field of Classification Search
CPC . C09B 69/045; C09B 29/0011; C09B 29/338; C09B 29/3626; C09B 29/3669; C09B 67/0083; C09D 11/328; C07C 215/08; C07C 215/12
See application file for complete search history.

(56) References Cited

U.S. PATENT DOCUMENTS

| | | | |
|---|---|---|---|
| 3,862,116 A | 1/1975 | Toji | |
| 4,399,068 A | 8/1983 | Kramer | |
| 4,685,933 A * | 8/1987 | Wolff | ................. C09B 67/0073 544/344 |
| 7,014,308 B2 | 3/2006 | Wachi et al. | |
| 7,686,851 B2 | 3/2010 | Schene | |
| 7,909,892 B2 | 3/2011 | Lautenbach et al. | |
| 2003/0210310 A1* | 11/2003 | Wachi | .................... C09D 11/40 347/100 |
| 2005/0071932 A1* | 4/2005 | Lautenbach | ........ C09B 67/0073 8/405 |

FOREIGN PATENT DOCUMENTS

| | | |
|---|---|---|
| CN | 1930248 A | 3/2007 |
| EP | 0030337 A2 | 6/1981 |
| JP | 1978-092734 A | 8/1978 |
| JP | 1981-090858 A | 7/1981 |
| JP | 1986-036369 A | 2/1986 |
| JP | 2003-292848 A | 10/2003 |
| JP | 2005-526866 A | 9/2005 |
| WO | 2003064539 A1 | 8/2003 |
| WO | WO 2005/087872 | * 9/2005 |

OTHER PUBLICATIONS

International Search Report as cited in the International Application PCT/EP2015/000662 dated Jul. 28, 2015.

* cited by examiner

*Primary Examiner* — Amina S Khan
(74) *Attorney, Agent, or Firm* — McBee Moore Woodward & Vanik IP, LLC

(57) ABSTRACT

The present invention relates to storage-stable dye salts, solutions and compositions thereof a process for their preparation and their use for dyeing and/or printing substrates.

14 Claims, No Drawings

STORAGE-STABLE DYE SOLUTIONS

CROSS REFERENCE TO RELATED APPLICATIONS

This application is a § 371 National Stage Application of PCT/EP2015/000662, filed Mar. 27, 2015, which claims priority to EP14001158.6, filed Mar. 28, 2014, and EP14001844.1, filed May 27, 2014.

FIELD OF THE INVENTION

The present invention relates to storage-stable dye salts, solutions, respectively compositions thereof, a process for their preparation and their use for dyeing and/or printing substrates.

BACKGROUND OF THE INVENTION

Dye compositions should have optimal stability so that they do not precipitate during transportation or in storage. Typically they should be stable for a prolonged period between 0 and 5° C., but also at around −20° C. and 50° C., respectively. Frozen dye compositions shall be stable after thawing and should not present any stability problems during pumping. Dye compositions containing precipitates can cause disruption in pumping or metering systems and lead to unacceptable machine shutdowns and costly cleaning and maintenance.

One problem of known aqueous dye solutions is the large amounts of added solubilizers, which lead to a high carbon content level in the dyehouse or paper mill effluents. This leads to effluents of high total organic carbon (TOC) and chemical oxygen demand (COD), and hence causes high water-treating costs.

Concentrated aqueous dye solutions are known. For example, EP0369940A2 discloses aqueous dye solutions comprising 7% to 30% by weight of a benzothiazole dye derivative together with 1 to 5 mol of a specific amine per mole of dye and also 10% to 25% by weight of an organic solubilizer.

WO03064539A1 discloses aqueous dye solutions comprising 5% to 30% by weight of a dye based on a benzothiazole derivative together with 0.05-5% of one or more additional, aromatic heterocycles (for example an additional benzothiazole derivative) and 1 to 5 mol of a base or of a mixture of bases per mole of dye. To produce the stable dye solutions, in both cases the free dye acids are isolated and stirred up with mixtures of water, standardizers and solubilizers.

Further reference can be made to EP 0 167 952, which discloses a number of concentrated aqueous solutions of dyes groups rendering those dyes water-soluble.

OBJECTS OF THE INVENTION

It is therefore an object of the present invention to provide storage-stable dye salts and compositions thereof.

SUMMARY OF THE INVENTION

This and other objects are achieved by the compound and composition according to the invention.

It has been surprisingly found that the storage stability of the dye composition according to the invention has been improved. In particular, the dye composition according to the invention is storage-stable at a temperature between −20° C. and 50° C., or between −15° C. and 40° C., or between −10° C. and 30° C., or between −5° C. and 20° C., or between −4° C. and 15° C., or between −3° C. and 10° C., or between −2° C. and 5° C., or between −1° C. and 4° C., or between 0° C. and 3° C., or between 1° C. and 2° C., for at least 1 day, or for at least 2 days, or for at least 3 days, or for at least 4 days, or for at least 5 days, or for at least 6 days, or for at least 1 week, or for at least 2 weeks, or up to 2 weeks.

In a first aspect, the invention provides a compound of formula (I)

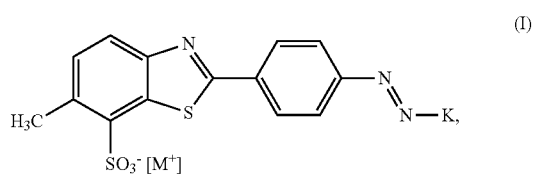

(I)

wherein
K is a coupling component,
M⁺ is a cation selected from the group consisting of triisopropanolamine cation, dimethylethanolamine cation, or mixtures thereof.

In one embodiment, K is selected from the group consisting of unsubstituted or substituted acetoacetanilide- (also called 1,3-di-oxo-butylaminobenzene), unsubstituted or substituted pyridine-, unsubstituted or substituted pyrazolone-, unsubstituted or substituted pyrimidine-, or unsubstituted or substituted acetoacetaminonaphthalene- (also called 1,3-di-oxo-butylaminonaphthalene) components.

In a second aspect, the invention provides a dye composition comprising
  (a) a compound of formula (I) according to the invention, and
  (b) at least one alkanolamine.

In one embodiment, the at least one alkanolamine is selected from the group consisting of triisopropanolamine, dimethylethanolamine, or mixtures thereof.

In one embodiment, the dye composition further comprises a solvent.

In one embodiment, the dye composition further comprises additives used in dye compositions selected from the group consisting of viscosity modifiers, surface tension modifiers, corrosion inhibitors, preservatives, kogation reducing additives, ionic or non-ionic surfactants, co-solvents, or mixtures thereof.

In one embodiment, the amount of (a) ranges from 1 to 30% by weight, or from 5 to 25% by weight, or from 10 to 20% by weight, or from 12.5 to 17.5% by weight, or from 14 to 16% by weight, and the amount of (b) ranges from 1 to 20% by weight, or from 2 to 10% by weight, or from 3 to 8% by weight, or from 4 to 6% by weight, based on the total weight of the dye composition, wherein the difference to 100% by weight is solvent and optionally further additives.

In one embodiment the dye composition according to the invention comprises, respectively essentially consists of
  (a) 14.5% by weight of a compound of the following formula

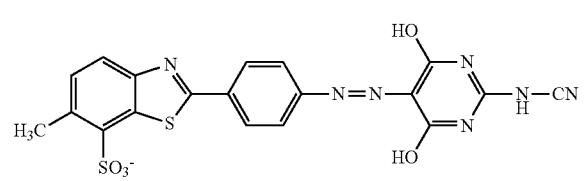

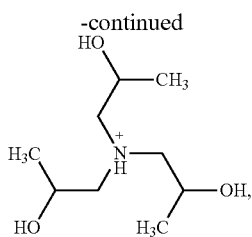

(b) 5% by weight of triisopropanolamine, and further 0.15% by weight of Nipacid BIT 20 and 80.35% by weight of water.

In a third aspect, the invention relates to a process for the manufacture of a dye composition according to the invention, wherein component (b) is added during the coupling of diazotized 2-(4-aminophenyl)-6-methylbenzothiazole-7-sulphonic acid onto a precursor H-K of coupling component K.

In a fourth aspect, the invention relates to a process for dyeing or printing a substrate, comprising contacting a dye composition according to the invention with said substrate.

In a fifth aspect, the invention relates to a substrate comprising at least one compound according to the invention or dye composition according to the invention.

In a sixth aspect, the invention relates to the use of a dye composition according to the invention or as prepared according to the invention for the preparation of a printing paste, ink, or a dyeing bath for printing or dyeing a substrate.

In one embodiment, the ink is a printing ink, e.g. an inkjet printing ink.

In a seventh aspect, the invention relates to the use of at least one alkanolamine for stabilizing a compound of formula (I) according to the invention.

In one embodiment, the alkanolamine is triisopropanolamine, dimethylethanolamine, or mixtures thereof.

In one embodiment, the alkanolamine reduces sedimentation and/or crystallization of a compound of formula (I) according to the invention at a temperature of 0° C., or 1° C., or 2° C., or 3° C., or 4° C., or 5° C., or 10° C., or 15° C., or 20° C., or 25° C., or 30° C., or 35° C., or 40° C., or 45° C., or 50° C. or at a temperature of −1° C., or −2° C., or −3° C., or −4° C., or −5° C., or −10° C., or −15° C., or −20° C. for at least 1 day, or for at least 2 days, or for at least 3 days, or for at least 4 days, or for at least 5 days, or for at least 6 days, or for at least 1 week, or for at least 2 weeks or up to 2 weeks.

DETAILED DESCRIPTION OF THE INVENTION

In a first aspect, the invention provides a compound of the general formula (I)

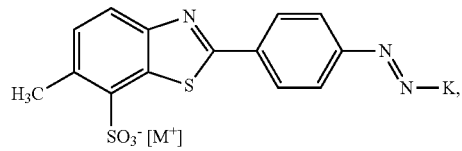

wherein
is a coupling component,
$M^+$ is a cation selected from the group comprising or consisting of triisopropanolamine cation, dimethylethanolamine cation, or mixtures thereof.

The compound of the above formula (I) may be present as a single compound. It may also be present in admixture with other dyes, e.g. other dyes of the structure of formula (I), however, comprising a cation being different from $M^+$ as defined above. In one embodiment, wherein $M^+$ is the dimethylethanolamine cation, the presence of one or more of 3-diethylamino-1-propylamine or 3-diethylamino-1-propylamine cation, 2-diethylaminoethanol or 2-diethylaminoethanol cation, and 2-(2-aminoethoxy)-ethanol or 2-(2-aminoethoxy)-ethanol cation is excluded. In a still further embodiment, wherein $M^+$ is the triisopropanolamine cation, the presence of triethanolamine or triethanolamine cation is excluded.

K may be selected from the group comprising or consisting of unsubstituted or substituted acetoacetanilide- (also called 1,3-di-oxo-butylaminobenzene), unsubstituted or substituted pyridine-, unsubstituted or substituted pyrazolone-, unsubstituted or substituted pyrimidine-, or unsubstituted or substituted acetoacetaminonaphthalene- (also called 1,3-di-oxo-butylaminonaphthalene) components.

The substituents of the substituted acetoacetanilide- (also called 1,3-di-oxo-butylaminobenzene), pyridone-, pyrazolone-, pyrimidine, or acetoacetaminonaphthalene (also called 1,3-di-oxo-butylaminonaphthalene) components are selected from the group consisting of —OH, —CN, —NH$_2$, —COO$^-$X$^+$, –SO$_3$$^-$X$^+$, wherein X$^+$ is H$^+$ or an alkanolamine cation, unsubstituted or substituted, linear or branched $C_{1-6}$ alkyl, unsubstituted or substituted, linear or branched $C_{1-6}$ alkoxy.

The term "alkanolamine cation" as used herein is equivalent to the term "alkanolammonium ion". Accordingly, "triisopropanolamine cation" is equivalent to "triisopropanolammonium ion", "dimethylethanolamine cation" is equivalent to "dimethylethanolammonium cation" and "3-diethylamino-1-propylamin cation" is equivalent to "3-diethylamino-1-propylammonium ion".

K can be derived from formula (II)

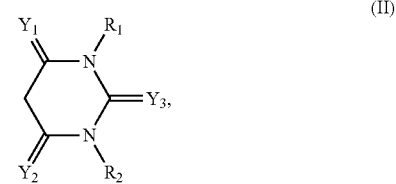

wherein
$Y_1$ and $Y_2$ are independently =O, =NH or =N—$C_{1-4}$ alkyl,
$Y_3$ is =O, =S, =N—H, =N—$C_{1-4}$ alkyl or =N—CN, and
$R_1$ and $R_2$ are independently H, unsubstituted or substituted, linear or branched $C_{1-6}$ alkyl, or unsubstituted or substituted linear or branched $C_{1-4}$ alkyl, or unsubstituted or substituted methyl, or unsubstituted or substituted phenyl.

The substituents of the substituted phenyl groups are selected from the group consisting of —OH, —CN, —NH$_2$, —COO$^-$X$^+$, —SO$_3$$^-$X$^+$, wherein X$^+$ is H$^+$ and/or an alkanolamine cation, unsubstituted or substituted, linear or branched $C_{1-6}$ alkyl, unsubstituted or substituted, linear or branched $C_{1-6}$ alkoxy, or mixtures thereof.

The above formula (II) is shown as indicated only in one tautomeric form for the coupling component K. However, the other tautomeric forms are also encompassed by this formula.

K can be derived from formula (III)

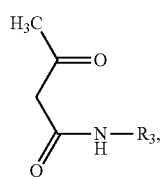

wherein $R_3$ is unsubstituted or substituted naphthyl, or unsubstituted or substituted phenyl.

The substituents of the substituted naphthyl group or substituted phenyl group are selected from the group consisting of, $-SO_3^-X^+$ (wherein $X^+$ is selected from the group consisting of $H^+$, alkanolamine cation, ammonium cation, alkali cation), unsubstituted or substituted, linear or branched $C_{1-6}$ alkyl, unsubstituted or substituted, linear or branched $C_{1-6}$ alkoxy, or mixtures thereof.

In particular, the substituents of the substituted naphthyl group or substituted phenyl group are $-SO_3^-X^+$ (wherein $X^+$ is $H^+$, $NH_4^+$, $Na^+$, $K^+$ or an alkanolamine cation), or methyl, or methoxy, or mixtures thereof.

The substituents of the substituted alkyl and alkoxy groups are selected from the group consisting of halogen, $-OH$, $-CN$, $-NH_2$, $-COO^-X^+$ and $-SO_3^-X^+$, wherein $X^+$ is $H^+$ and/or an alkanolamine cation.

In particular, K may be selected from

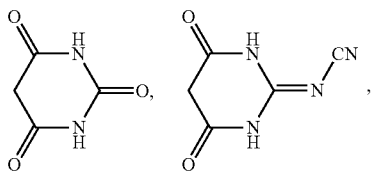

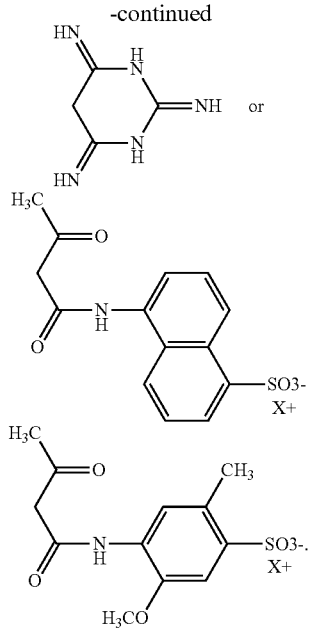

The compound of formula (I) consists of cation $M^+$ and an anion having the formula

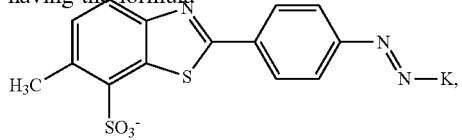

wherein K is a coupling component.

In particular, the compound of formula (I) may be selected from the group comprising or consisting of (compounds of formula (I) shown below also encompass the respective tautomeric forms thereof):

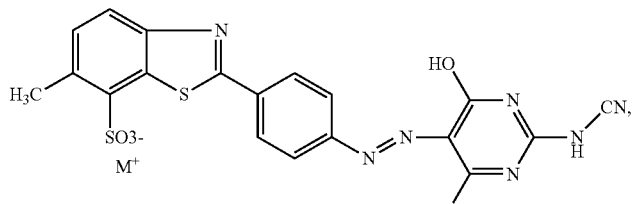

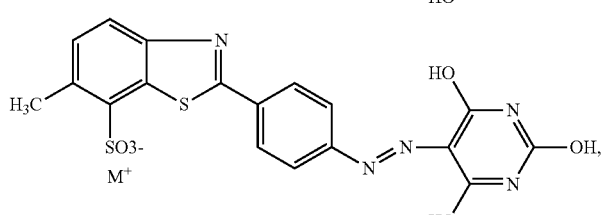

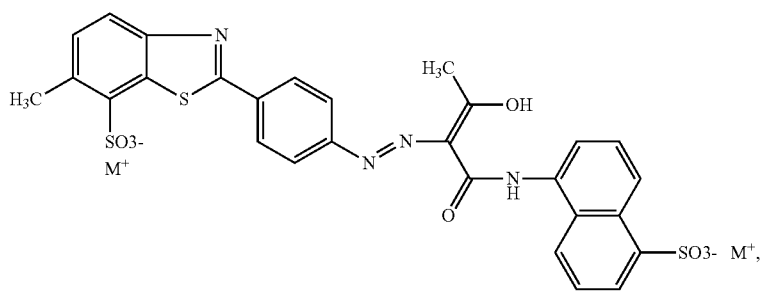

-continued

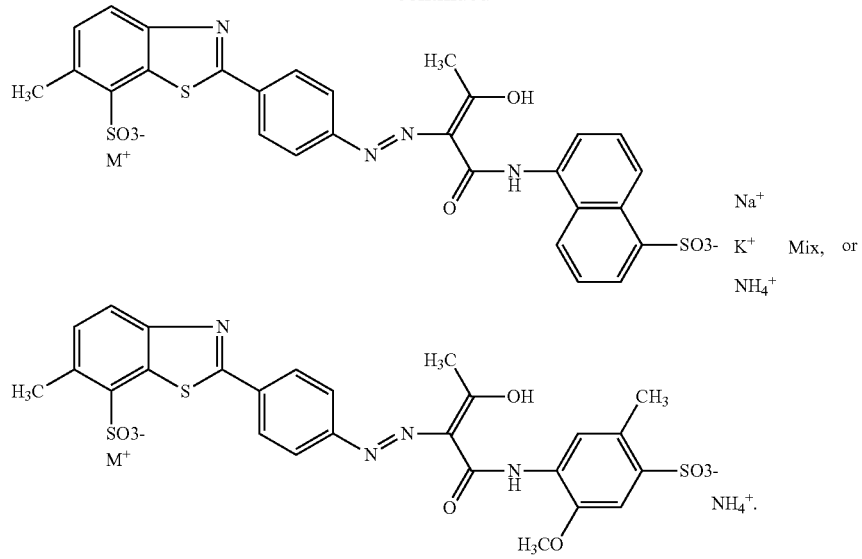

The cation $M^+$ of the compound of formula (I) may be selected from group comprising or consisting of

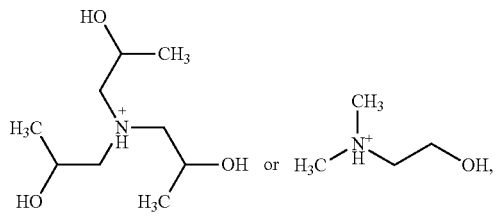

or mixtures thereof.

In case the cation $M^+$ of the compound of formula (I) is a mixture of triisopropanolamine cations and dimethylethanolamine cations, the molar ratio of triisopropanolamine cations and dimethylethanolamine cations ranges from 1:0.1 to 1:10, or from 1:0.5 to 1:5, or from 1:1 to 1:2.5, or from 1:1.5 to 1:2, or from 1:2.5 to 1:5.

In a second aspect, the invention relates to a dye composition comprising
(a) a compound of formula (I) according to the invention, and
(b) at least one alkanolamine.

The at least one alkanolamine is selected from the group comprising or consisting of mono-, di-, or tri-$C_{1-4}$ alkylamines, mono-, di- or tri-$C_{2-4}$ hydroxyalkylamines or mono-, di- or tri-$C_{2-4}$ hydroxyalkyl-$C_{1-4}$alkylamines or mixtures thereof. In particular, the dye composition according to the invention may comprise triisopropanolamine, dimethylethanolamine, or a mixture of triisopropanolamine or dimethylethanolamine.

In general, the dye composition according to the invention is present as a solution. Accordingly, the dye composition may further comprise a solvent.

The solvent may be selected from the group comprising or consisting of water, in particular demineralized water, an organic solvent which is different from the already present alkanolamine or mixture of alkanolamines, or mixtures thereof.

Within the subject composition, the compound of the above formula (I) may be present as the sole dye component. It may also be present in the admixture with other dyes, e.g. other dyes of the structure of formula (I), however, comprising a cation being different from $M^+$ as defined above.

In one embodiment, wherein $M^+$ is the dimethylethanolamine cation, the presence of one or more of 3-diethylamino-1-propylamin, 2-diethylaminoethanol, and 2-(2-aminoethoxy)-ethanol, either in the form of a cation or as component (b) is excluded.

In one embodiment, wherein $M^+$ is the triisopropanolamin cation, the presence of triethanolamine in the form of a cation is excluded. In another embodiment, wherein $M^+$ is the triisopropanolamin cation, the presence of triethanolamine as component (b) is excluded.

If the dye composition comprises dimethylethanolamine as component (b), the presence of 3-diethylamino-1-propylamin, or 2-diethylaminoethanol or 2-(2-aminoethoxy)-ethanol may be excluded.

The organic solvent present in the mixture of water and organic solvent may be a water-miscible organic solvent or a mixture of such solvents. In particular, the organic solvent is different from triisopropanolamine or dimethylethanolamine.

Water-miscible organic solvents include $C_{1-4}$-alkanols, or methanol, ethanol, n-propanol, isopropanol, n-butanol, sec-butanol, tert-butanol, n-pentanol, cyclopentanol and cyclohexanol, benzyl alcohol; linear amides, or dimethylformamide or dimethylacetamide, ketones and ketone-alcohols, or acetone, methyl ether ketone, cydohexanone and diacetone alcohol; water-miscible ethers, or tetrahydrofuran and dioxane, diols, or diols having from 2 to 12 carbon atoms, for example pentane-1,5-diol, ethylene glycol, propylene glycol, butylene glycol, pentylene glycol, hexylene glycol and thiodiglycol and oligo- and poly-alkyleneglycols, or diethylene glycol, triethylene glycol, polyethylene glycol and polypropylene glycol; trials, or glycerol and 1,2,6-hexanetriol, mono-$C_{1-4}$-alkyl ethers of diols, or mono-$C_{1-4}$-alkyl ethers of diols having 2 to 12 carbon atoms, especially 2-methoxyethanol, 2-(2-methoxyethoxy)ethanol, 2-(2-ethoxyethoxy)-ethanol, 2-(2-(2-methoxyethoxy)ethoxy] ethanol, 2-[2-(2-ethoxyethoxy)-ethoxy]-ethanol and ethyleneglycol monoallylether, cyclic amides, or 2-pyrrolidone, N-methyl-2-pyrrolidone, N-ethyl-2-pyrrolidone, caprolactam and 1,3-dimethylimidazolidone, cyclic esters, or caprolactone, sulfoxides, or dimethyl sulfoxide and sulfolane.

Further water-soluble organic solvents are cyclic amides, especially 2-pyrrolidone, N-methyl-pyrrolidone and N-ethyl-pyrrolidone, diols, especially 1,5-pentane diol, ethyleneglycol, thiodiglycol, diethyleneglycol and triethyleneglycol, and mono-$C_{1-4}$-alkyl and $C_{1-4}$-alkyl ethers of diols, or mono-$C_{1-4}$-alkyl ethers of diols having 2 to 12 carbon atoms, especially 2-methoxy-2-ethoxy-2-ethoxyethanol.

In general, the amount of component (a) in the dye composition ranges from 1 to 35% by weight, or from 2 to 30% by weight, or from 5 to 25% by weight, or from 10 to 20% by weight, or from 12.5 to 17.5% by weight, or from 14 to 16% by weight, based on the total weight of the dye composition. The amount of component (b) in the dye composition generally ranges from more than 0% to 20% by weight, or from 1 to 15% by weight, or from 2 to 10% by weight, or from 3 to 8% by weight, or from 4 to 6% by weight, based on the total weight of the dye composition. The difference to 100% by weight is solvent and optionally further additives.

In case component (b) is a mixture of triisopropanolamine and dimethylethanolamine, the molar ratio of triisopropanolamine:dimethylethanolamine can be chosen arbitrarily. Generally, the molar ratio ranges from 1:0.1 to 1:10, or from 1:0.5 to 1:5, or from 1:1 to 1:2.

In one embodiment, the dye composition comprises 14.5% by weight of the compound

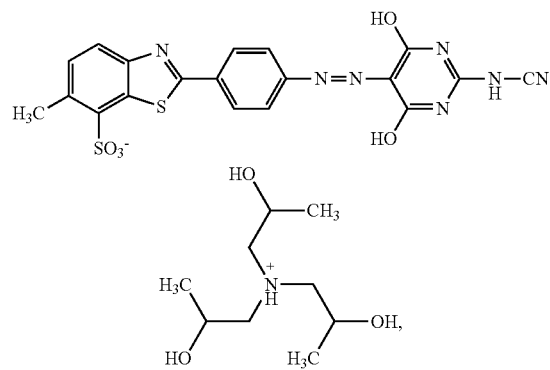

and 5% by weight of triisopropanolamine.

In a further embodiment, the dye composition comprises 14.5% by weight of the compound

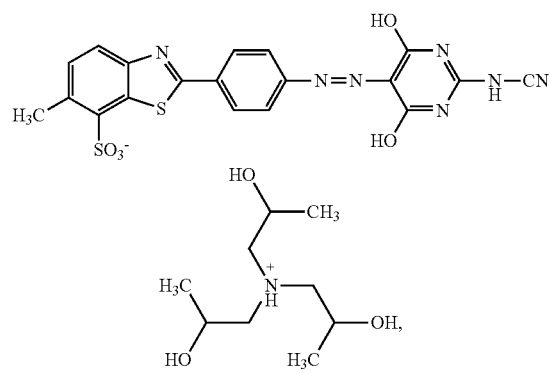

and 4.3% by weight of triisopropanolamine.

In one embodiment, the dye composition comprises 14.5% by weight of the compound

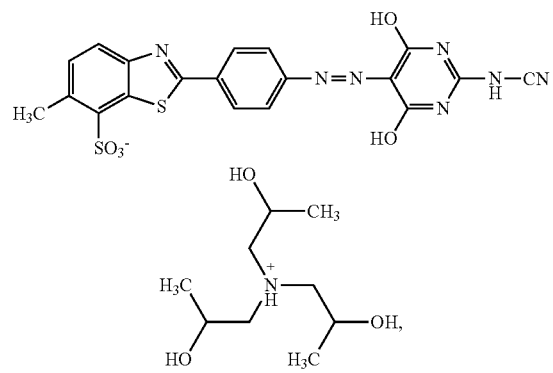

and 1% by weight of triisopropanolamine.

In a further embodiment, the dye composition comprises 17.0% by weight of the compound

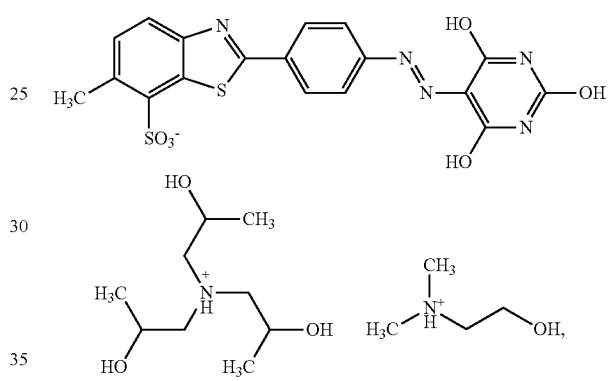

wherein the molar ratio of triisopropanolamine cations to dimethylethanolamine cations is 1:5, and 0.12% by weight of triisopropanolamine and 0.27% by weight of dimethylethanolamine.

In a further embodiment, the dye composition comprises 17.4% by weight of the compound

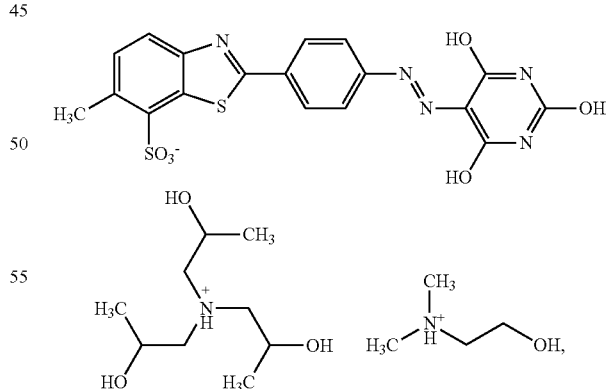

wherein the molar ratio of triisopropanolamine cations to dimethylethanolamine cations is 1:2.5, and 0.2% by weight of triisopropanolamine and 0.1% by weight of dimethylethanolamine.

In a further embodiment, the dye composition comprises 14.5% by weight of the compound

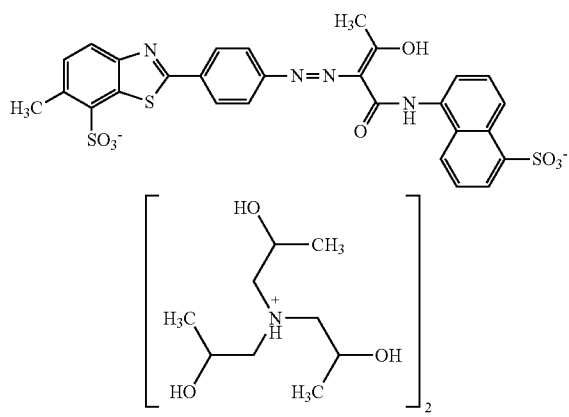

and 1.2% by weight of triisopropanolamine.

In a further embodiment, the dye composition comprises 12.1% by weight of the compound

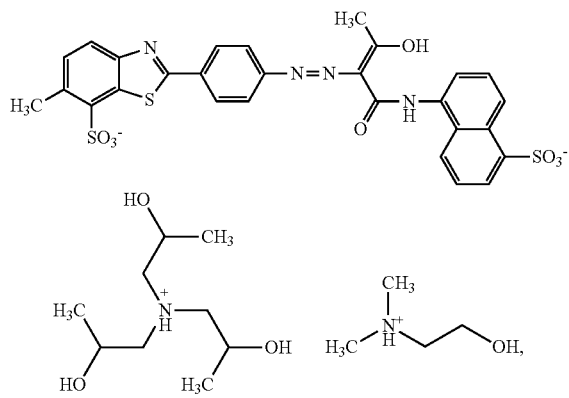

wherein the molar ratio of triisopropanolamine cations to dimethylethanolamine cations is 1:5, and 0.4% by weight of triisopropanolamine and 0.9% by weight of dimethylethanolamine.

In a further embodiment, the dye composition comprises 14.5% by weight of the compound

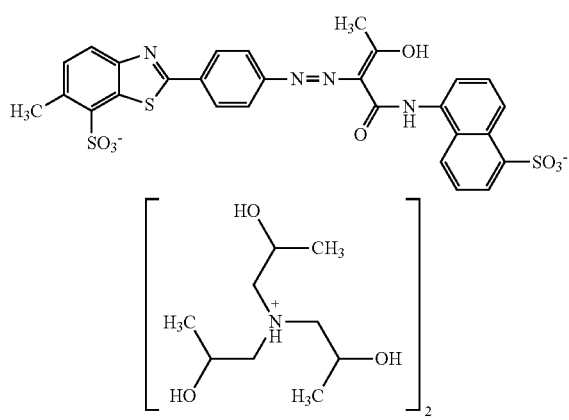

and 1.6% by weight of triisopropanolamine.

In a further embodiment, the dye composition comprises 14.5% by weight of the compound

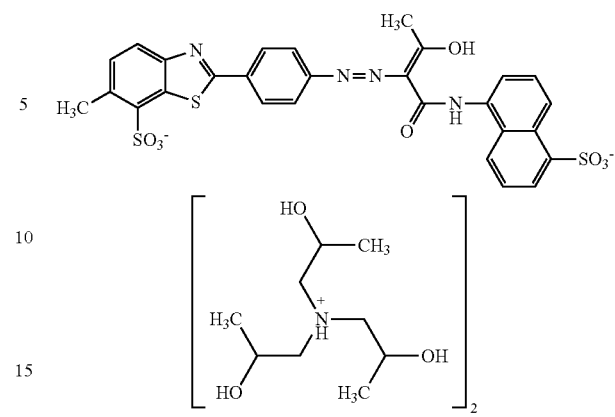

and 2.4% by weight of triisopropanolamine.

In a further embodiment, the dye composition comprises 19.9% by weight of the compound

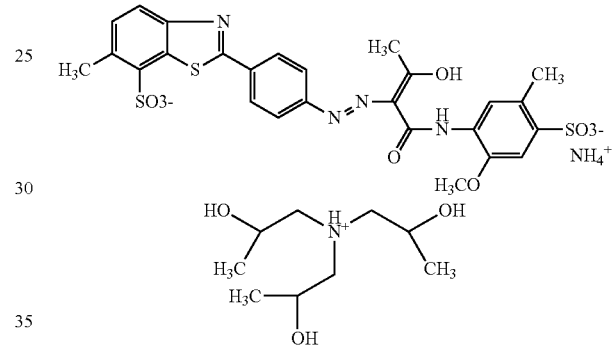

and 5.5% by weight of triisopropanolamine.

The dye composition may further comprise one or more additives conventionally used in dye compositions. Said additives may be selected from the group comprising or consisting of viscosity modifiers, surface tension modifiers, corrosion inhibitors, preservatives, kogation reducing additives, ionic or non-ionic surfactants, co-solvents, or mixtures thereof.

Examples of additives are urea, 1,2-benzisothiazolin-3-one (Nipacid BIT 20, CAS-Nr. 2634-33-5), glutardialdehyde or mixtures thereof.

The term "preservative" as used herein is to be understood as a chemical substance capable of detering, rendering harmless, or exerting a controlling effect on any harmful organisms, such Gram-positive or Gram-negative bacteria, yeasts or fungi, by chemical or biological means. The preservative may be a biocide. In general, any biocide can be used as a preservative in the compositions of the present invention. However, preference is given to using biocides having FDA approval. Suitable biocides are, for example, 3-thiazolone derivatives, or alkylated and/or chlorinated 3-thiazolone derivatives such as 1,2-benzisothiazolin-3-one (Nipacid BIT 20, CAS-Nr. 2634-33-5), glutaraldehyde or mixtures thereof. The amount of biocide generally ranges from 0.01 to 10% by weight, or from 0.1 to 1% by weight. Typically, the biocide is added to the dye composition in an amount of up to 0.15% by weight (per ready-produced dye composition).

If glutardialdehyde is present in the dye composition, the amount of glutardialdehyde generally ranges from 0.01 to 10% by weight, or from 0.1 to 1% by weight.

The term "co-solvent" as used herein is to be understood as additive that is added to the dye composition to enhance the power of the solvent. The co-solvent may be urea.

If co-solvent is present in the dye composition, the amount of co-solvent, in particular urea, generally ranges from 1 to 30% by weight, or from 2 to 25% by weight, or from 5 to 20% by weight, or from 10 to 15% by weight.

In one embodiment, the dye composition comprises:
14.5% by weight of the compound

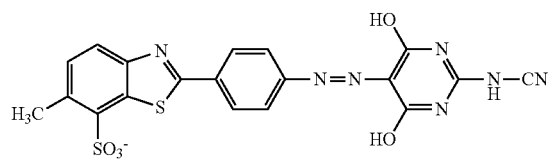

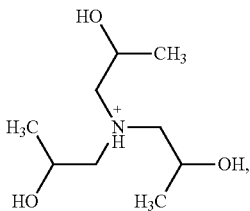

5% by weight of triisopropanolamine, and
0.15% by weight Nipacid BIT 20.
In a further embodiment, the dye composition comprises:
14.5% by weight of the compound

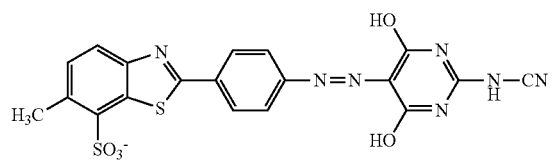

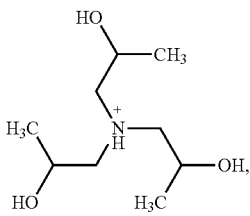

4.3% by weight of triisopropanolamine, and
0.15% by weight Nipacid BIT 20.
In a further embodiment, the dye composition comprises
17.0% by weight of the compound

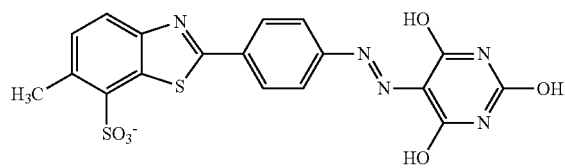

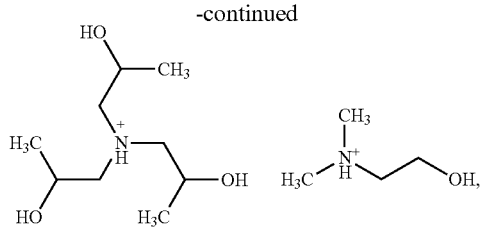

wherein the molar ratio of triisopropanolamine cations to dimethylethanolamine cations is 1:5,
0.12% by weight of triisopropanolamine,
0.27% by weight of dimethylethanolamine,
14.9% by weight of urea, and
0.15% by weight of Nipacid BIT 20.
In a further embodiment, the dye composition comprises:
17.4% by weight of the compound

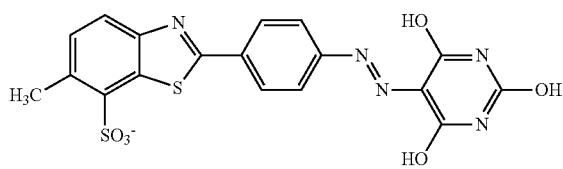

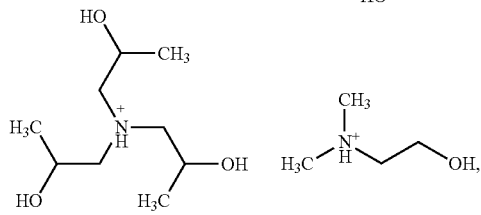

wherein the molar ratio of triisopropanolamine cations to dimethylethanolamine cations is 1:2.5,
0.2% by weight of triisopropanolamine,
0.1% by weight of dimethylethanolamine,
12.6% by weight of urea,
0.15% by weight of Nipacid BIT 20.
In a further embodiment, the dye composition comprises:
14.5% by weight of the compound

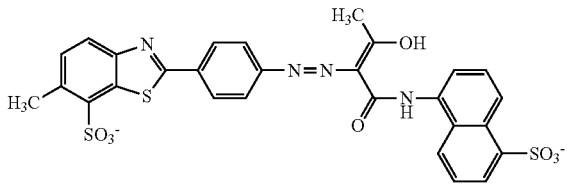

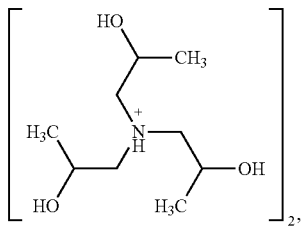

1.2% by weight of triisopropanolamine,
0.15% by weight of Nipacid BIT 20, and
0.1% by weight of glutardialdehyde.

In a further embodiment, the dye composition comprises:
12.1% by weight of the compound

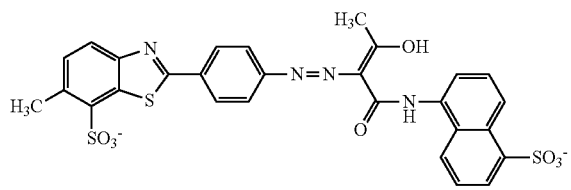

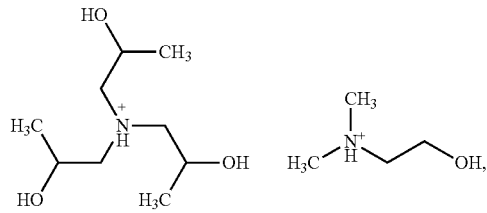

wherein the molar ratio of triisopropanolamine cations to dimethylethanolamine cations is 1:5,
0.4% by weight of triisopropanolamine,
0.9% by weight of dimethylethanolamine,
0.15% by weight of Nipacid BIT 20, and
0.1% by weight of glutardialdehyde.

In a further embodiment, the dye composition comprises:
14.5% by weight of the compound

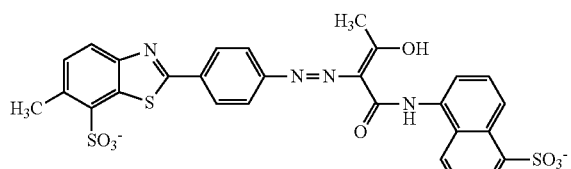

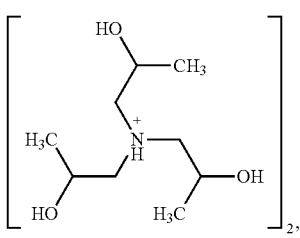

1.6% by weight of triisopropanolamine,
0.15% by weight of Nipacid BIT 20, and
0.1% by weight of glutardialdehyde.

In a further embodiment, the dye composition comprises:
14.5% by weight of the compound

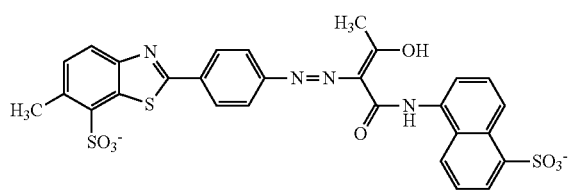

-continued

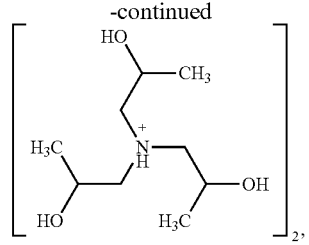

2.4% by weight of triisopropanolamine,
0.15% by weight of Nipacid BIT 20, and
0.1% by weight of glutardialdehyde.

In a further embodiment, the dye composition comprises:
19.9% by weight of the compound

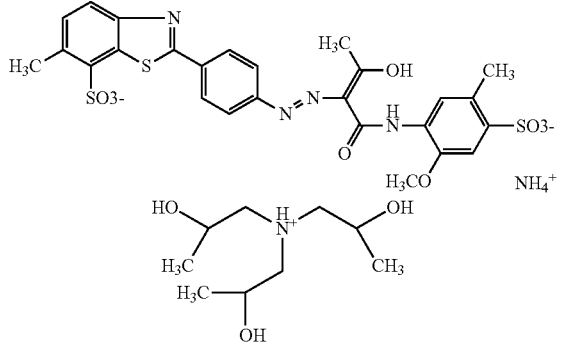

5.5% by weight triisopropanolamine, and
0.15% by weight Nipacid BIT 20.

The dye composition according to the invention is useful as ink, or printing ink, e.g. an inkjet printing ink, printing paste, or in a dyeing bath for dyeing a substrate.

In a third aspect, the invention relates to a process for the manufacture of a dye composition according to the invention.

In general, the dye composition according to the invention is produced by adding component (b) during the coupling of diazotized 2-(4-aminophenyl)-6-methylbenzothiazole-7-sulphonic acid onto a precursor H-K of coupling component K. If necessary, the dye composition is subsequently filtered and/or diluted. Furthermore it is possible to add additives or solvents or an excess of alkanolamine subsequently.

The term "precursor H-K of coupling component K" is to be understood as a nucleophilic coupling component, in which, during coupling onto the activated diazonium compound, the proton is removed.

Without being bound to theory, it is believed that the formation of [M$^+$] occurs during the coupling of diazotized 2-(4-aminophenyl)-6-methylbenzothiazole-7-sulphonic acid onto the precursor H-K of coupling component K, stated differently, the formation of [M$^+$] only occurs in cases where the alkanolamine is present in admixture with the precursor H-K. It is also believed that addition of alkanolamine after coupling is not associated with the formation of further alkanolamine salts.

In a fourth aspect, the invention relates to a process for dyeing or printing a substrate, comprising contacting of a dye composition according to the invention with said substrate.

The dye composition according to the invention is useful as dyestuffs, especially for the coloration of inks for inkjet printing. The dye composition is also suitable for dyeing and printing in a conventional manner. The dye composition exhibits a high solubility in aqueous media and provides dyeings which exhibit improved high light fastness and wet/washing fastness when applied on a substrate or incorporated into inks for inkjet printing.

The term "dyeing" as used herein encompasses all processes of adding color to a substrate, in particular to a textile or paper. Dyeing is normally carried out in a dyebath comprising at least one dye composition. During the dyeing process, the dye is applied on the whole substrate such that the substrate is at least partially, preferably completely soaked with the dye. Furthermore, the dye can be added, e.g. to the paper pulp.

The dyeing process may be an exhaust-dyeing process, in which temperatures within the range of from 40 to 100° C., or 50 to 80° C. are used. The term "exhaust dyeing process" as used herein is to be understood as a process in which the dye is gradually transferred from a relatively large volume dyebath to the organic substrate being dyed over a relatively long period of time (see A Review of Textile Dyeing Processes, Perkins W. S, 1991. Textile Chemist & Colorist vol. 23(8) 23-27).

The dyeing process may be a continuous dyeing process. The term "continuous dyeing process" as used herein is to be understood as a process in which the substrate to be dyed is fed continuously into a dye range. Examples of a continuous dyeing process are pad-steam process or pad-dry process.

The term "printing" as used herein is to be understood as a process to reproduce text or images on a substrate, in particular on paper or textiles. During the printing process, dyes are applied on the substrate localizedly. The printing process may be an inkjet printing process, which is a non-impact printing technique in which droplets of ink are ejected through a fine nozzle onto a substrate without bringing the nozzle into contact with the substrate.

The term "substrate" as used herein encompasses all substrates of natural or synthetic origin. The substrate may be present in the form of a textile, (i.e. material consisting of or comprising natural or synthetic polyamides such as wool, silk and all nylon types, or cotton). The term "substrate" also encompasses hydroxy- or nitrogen-containing materials as well as cellulosic fibers.

Further examples for the form/appearance of the substrate are yarn, woven fabric, loop-formingly knitted fabric carpet comprising or consisting of an organic substrate, e.g. natural or synthetic polyamides (for example wool, silk and all nylon types), polyurethanes, cellulose as well as hydrophobic and non-absorbent substrates, for example plastics, metal and glass.

Substrates for dyeing may be leather and fibrous materials, which comprise natural or synthetic polyamides and, particularly, natural or regenerated cellulose such as cotton, viscose and spun rayon. Further substrates for dyeing are textiles comprising cellulosic fibers, in particular cotton.

The composition according to the invention is particularly useful for dyeing paper.

In general, substrates for printing are paper, plastic, textiles, metal, glass, or an overhead projector slide.

The term "contacting", respectively "contacting a dye composition with a substrate" as used in the context of the present invention means that the substrate to be dyed or to be printed is partly or completely dyed or printed with the respective dye composition according to the invention.

Dyeing or printing may be carried out in accordance with known methods conventional used in the dyestuff field.

The inkjet printer generally applies the ink to the substrate in the form of droplets which are ejected through a small orifice onto the substrate. Inkjet printers may be piezoelectric inkjet printers and thermal inkjet printers. In thermal inkjet printers, programmed pulses of heat are applied to the ink in a reservoir by means of a resistor adjacent to the orifice, thereby causing the ink to be ejected in the form of small droplets directed towards the substrate during relative movement between the substrate and the orifice. In piezoelectric inkjet printers the oscillation of a small crystal causes ejection of the ink from the orifice.

The process for printing an image on a substrate comprises applying thereto an ink comprising a dye composition according to the invention by means of an inkjet printer.

The invention also relates to an inkjet printer cartridge containing an ink, characterized in that the ink comprises a dye composition according to the invention.

In a fifth aspect, the invention relates to a substrate, comprising at least one dye composition according to the invention.

In general, the invention relates to a substrate, obtainable by a process for dyeing or printing said substrate, comprising contacting of a dye composition according to the invention with said substrate.

In a sixth aspect, the invention relates to the use of a dye composition according to the invention or as prepared according to the invention for the preparation of a printing paste, ink, or a dyeing bath for printing or dyeing a substrate.

According to this aspect, the invention also relates to an ink or printing ink or inkjet printing ink or printing paste or dyeing bath for printing or dyeing a substrate, comprising the compound of formula (I) according to the invention or the dye composition according to the invention during storage.

The ink may be a printing ink, or an inkjet printing ink.

In a seventh aspect, the invention relates to the use of at least one alkanolamine for stabilizing a dye composition according to the invention during storage.

The term "stabilize" or "stabilizing" as used herein is to be understood as increasing the storage-stability of a dye composition. The terms "stability", "storage-stability", "stable" or "storage-stable" as used herein means maintaining the homogeneity of a dye composition over a certain temperature range during a certain time.

In general, the alkanolamine is triisopropanolamine, dimethylethanolamine, or mixtures thereof.

In general, a dye composition can be considered stable or storage-stable when neither sedimentation nor crystallization is observed at a certain temperature or a temperature range during a certain time, in particular at a temperature of 0° C., or 1° C., or 2° C., or 3° C., or 4° C., or 5° C., or 10° C., or 15° C., or 20° C., or 25° C., or 30° C., or 35° C., or 40° C., or 45° C., or 50° C. or at a temperature of −1° C., or −2° C., or −3° C., or −4° C., or −5° C., or −10° C., or −15° C., or −20° C. for at least 1 day, or for at least 2 days, or for at least 3 days, or for at least 4 days, or for at least 5 days, or for at least 6 days, or for at least 1 week, or for at least 2 weeks or up to 2 weeks.

EXAMPLES

The invention is further illustrated by the following examples in which all parts and percentages are by weight unless otherwise stated and all temperatures are given in degrees Centigrade.

Preparation Example 83.5 g of 2-(4-aminophenyl)-6-methylbenzothiazole-7-sulphonic acid (titer=76.8%) are dissolved in dilute aqueous sodium hydroxide solution, prepared from 600 g of water and 22.4 ml of 30% caustic soda, and admixed with 36.2 ml of 40% sodium nitrite solution. For diazotation, this solution is pumped into a mixture of 50 g of ice and 60 ml of 30% hydrochloric acid and additional 263.0 g ice are added. The resulting suspension is filtered and the presscake washed with dilute hydrochloric acid.

Subsequently, 54.2 g of 2-cyanimino-4,6-dihydroxypyrimidine (titer=59.5%) and 188.8 g of the diazo presscake are introduced into a mixture of 200 ml of deionized water and 100 g triisopropanolamine (titer=85%) and stirred up therein, before further addition of 200 ml deionized water. The solution is filtered and deionized water is added to a final mass of 930 g.

All Examples 1 to 6 as presented subsequently are prepared according to the presented method. Example 4 and 5 are synthesized via coupling on 1-acetoacetyl-aminonaphthalin-5-sulfonic acid (free acid). Example 6 is synthesized via coupling on 1-acetoacetylamino-2-methoxy-5-methyl-4-sulfonic acid in form of its ammonium salt.

Example 1

A composition comprising 14.5% by weight of a compound of the following formula

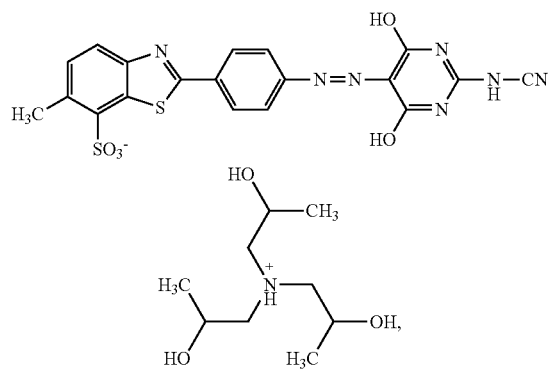

5% by weight of triisopropanolamine, 0.15% by weight of Nipacid BIT 20 and 80.35% by weight of water was subjected to an oven test (2 weeks at 50° C.), a fridge test (2 weeks at 3° C.) and a freezer test (2 days at −20° C.) and visually and microscopically inspected thereafter. No sedimentation or crystallization was observed demonstrating that the dye composition comprising a compound of formula (I) as triisopropanolamine salt is storage-stable.

Example 2

A composition comprising 17.0% by weight of the compound

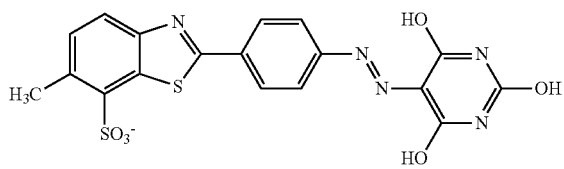

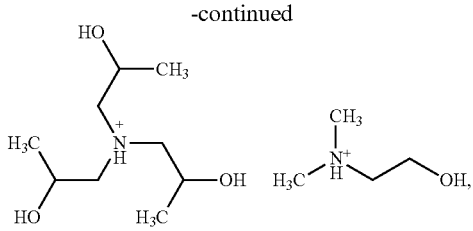

with a molar ratio of triisopropanolamine cations to dimethylethanolamine cations of 1:5, 0.12% by weight of triisopropanolamine, 0.27% by weight of dimethylethanolamine, 14.9% by weight of urea, 0.15% by weight of Nipacid BIT 20, and 67.56% by weight of water was subjected to an oven test (2 weeks at 50° C.) and a fridge test (2 weeks at 3° C.) and visually and microscopically inspected thereafter. No sedimentation or crystallization was observed demonstrating that the dye composition comprising a compound of formula (I) as mixed triisopropanolamine/dimethylethanolamine salt is storage-stable.

Example 3

A composition comprising 17.4% by weight of the compound

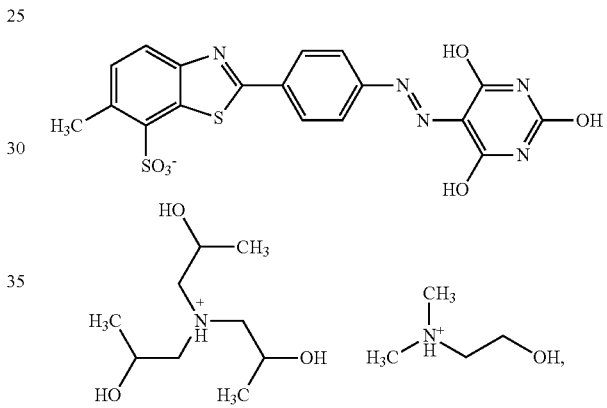

wherein the molar ratio of triisopropanolamine cations to dimethylethanolamine cations is 1:2.5, 0.2% by weight of triisopropanolamine, 0.1% by weight of dimethylethanolamine, 12.6% by weight of urea, 0.15% by weight of Nipacid BIT 20, and 69.55% by weight of water was subjected to an oven test (2 weeks at 50° C.) and a fridge test (2 weeks at 3° C.) and visually and microscopically inspected thereafter. No sedimentation or crystallization was observed demonstrating that the dye composition comprising a compound of formula (I) as mixed triisopropanolamine/dimethylethanolamine salt is storage-stable.

Example 4

A composition comprising 14.5% by weight of a compound of the following formula

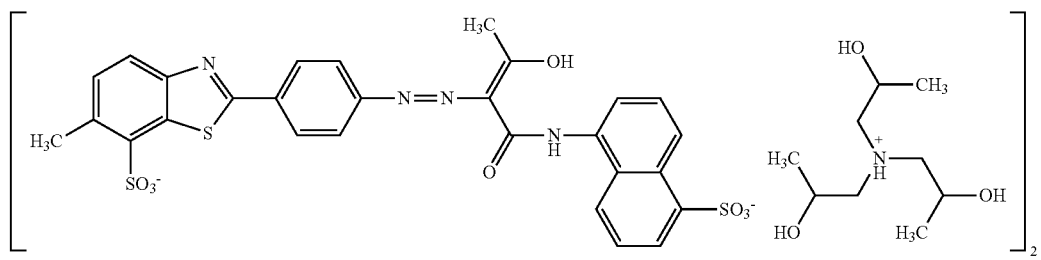

1.6% by weight of triisopropanolamine, 0.15% by weight of Nipacid BIT 20, 0.1% by weight of glutardialdehyde and 83.65% by weight of water was subjected to an oven test (2 weeks at 50° C.), a fridge test (2 weeks at 3° C.) and a freezer test (2 days at −20° C.) and visually and microscopically inspected thereafter. No sedimentation or crystallization was observed demonstrating that the dye composition comprising a compound of formula (I) as triisopropanolamine salt is storage-stable.

Example 5

A composition comprising 12.1% by weight of a compound of the following formula

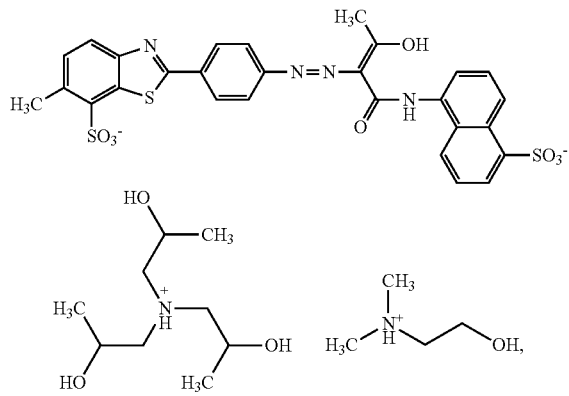

with a molar ratio of triisopropanolamine cations to dimethylethanolamine cations of 1:5, 0.4% by weight of triisopropanolamine, 0.9% by weight of dimethylethanolamine, 0.15% by weight of Nipacid BIT 20, 0.1% by weight of glutardialdehyde and 86.35% by weight of water was subjected to an oven test (2 weeks at 50° C.), a fridge test (2 weeks at 3° C.) and a freezer test (2 days at −20° C.) and visually and microscopically inspected thereafter. No sedimentation or crystallization was observed demonstrating that the dye composition comprising a compound of formula (I) as mixed triisopropanolamine/dimethylethanolamine salt is storage-stable.

Example 6

A composition comprising 19.9% by weight of a compound of the following formula

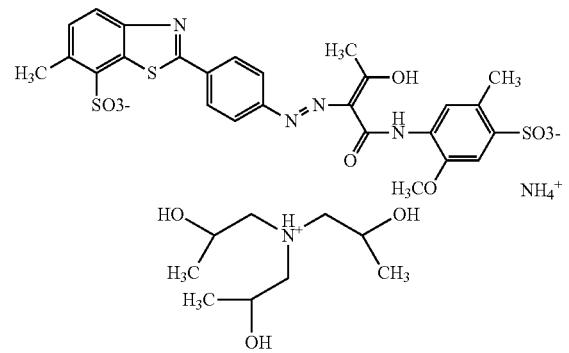

dissolved in 5.5% by weight of triisopropanolamine, 0.15% by weight of Nipacid BIT 20 and 75.45% by weight of water was subjected to an oven test (2 weeks at 50° C.), a fridge test (2 weeks at 3° C.) and visually and microscopically inspected thereafter. No sedimentation or crystallization was observed demonstrating that the dye composition comprising a compound of formula (I) as triisopropanolamine salt is storage-stable.

Example 7

Comparative Example

A composition comprising 18.6% by weight of a compound of the following formula

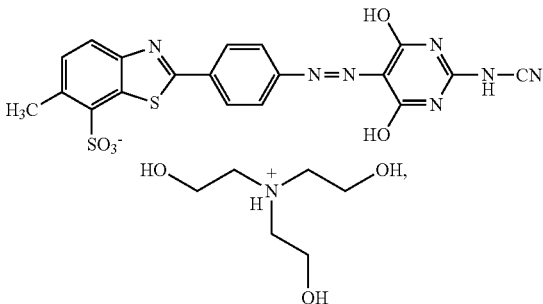

dissolved in 6.9% by weight of triethanolamin and 80.5% by weight of water was subjected to an oven test (2 weeks at 50° C.), a fridge test (2 weeks at 3° C.) and a freezer test (2 days at −20° C.) and visually and microscopically inspected thereafter. The results are shown in table 1.

Example 8 (Comparative Example)

A composition comprising 18.6% by weight of a compound of the following formula

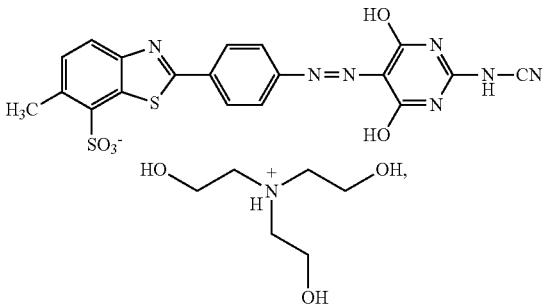

dissolved in 6.9% by weight of triethanolamin, 0.15% by weight of Nipacid BIT 20 and 80.35% by weight of water was subjected to an oven test (2 weeks at 50° C.), a fridge test (2 weeks at 3° C.) and a freezer test (2 days at −20° C.) and visually and microscopically inspected thereafter. The results are shown in table 1.

TABLE 1

| Example | Treatment | Visual assessment | Examination under microscope |
| --- | --- | --- | --- |
| 7 | Untreated | Thin layer at bottom | Homogeneous distribution of some fine crystals |
|   | Oven test | Thin layer at bottom | Homogeneous distribution of some fine crystals |
|   | Fridge test | Approx. 3 cm of sediment | Strong and even formation of crystals and agglomerations |
|   | Freezer test | Approx. 1 cm of sediment | Strong and even formation of crystals and agglomerations |

TABLE 1-continued

| Example | Treatment | Visual assessment | Examination under microscope |
|---|---|---|---|
| 8 | Untreated | Thin layer at bottom | Homogeneous distribution of some fine crystals |
|  | Oven test | Thin layer at bottom | Homogeneous distribution of some fine crystals |
|  | Fridge test | Approx. 3 cm of sediment | Strong and even formation of crystals and agglomerations |
|  | Freezer test | Approx. 1 cm of sediment | Strong and even formation of crystals and agglomerations |

The observations shown in table 1 demonstrate that a dye composition comprising a benzothiazole dye as triethanolamine salt is less storage-stable compared to the dye compositions according to the invention. Furthermore, it can be concluded that the presence of biocide does not have any effect on the stability of the dye composition.

The invention claimed is:

1. A dye composition, comprising
(a) 14.5% by weight of a compound of formula

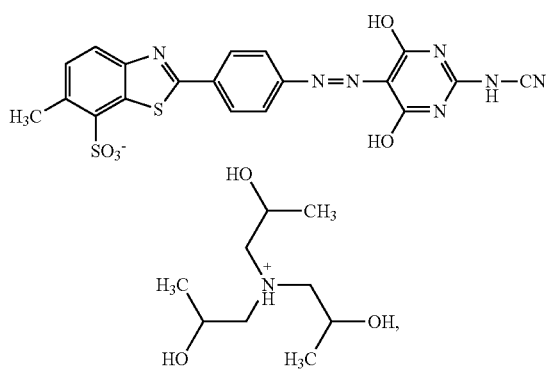

(b) 5% by weight of triisopropanolamine, and further 0.15% by weight of 1,2-benzisothiazolin-3-one and 80.35% by weight of water.

2. The dye composition according to claim 1, wherein presence of triethanolamine or triethanolamine cation is excluded.

3. A dye composition according to claim 1, comprising wherein the composition does not include compounds of formula (I) where M+ is a triethanol amine cation

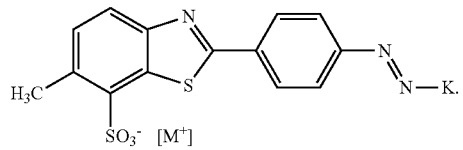

4. A dye composition according to claim 3, further comprising a solvent.

5. A dye composition according to claim 3, further comprising one or more additives used in a dye composition selected from the group consisting of viscosity modifiers, surface tension modifiers, corrosion inhibitors, preservatives, kogation reducing additives, ionic or non-ionic surfactants, co-solvents, or mixtures thereof.

6. The dye composition according to claim 1, wherein the alkanolamine (b) reduces sedimentation and/or crystallization of the compound (a) at a temperature between −20° C. and 50° C. for at least 1 day.

7. The dye composition according to claim 6, wherein the alkanolamine (b) reduces sedimentation and/or crystallization of the compound (a) at a temperature between 0° C. and 3° C.

8. The dye composition according to claim 6, wherein the alkanolamine (b) reduces sedimentation and/or crystallization of the compound (a) for at least 2 days.

9. The dye composition according to claim 6, wherein the alkanolamine (b) reduces sedimentation and/or crystallization of the compound (a) for at least 6 days.

10. The dye composition according to claim 6, wherein the alkanolamine (b) reduces sedimentation and/or crystallization of the compound (a) for at least 2 weeks.

11. Process for the manufacture of a dye composition as claimed in claim 3, wherein component (b) is added during the coupling of diazotized 2-(4-aminophenyl)-6-methylbenzothiazole-7-sulphonic acid onto a precursor H-K of coupling component K, wherein the precursor H-K of coupling component K is a nucleophilic coupling component, in which a proton is removed during coupling onto an activated diazonium compound.

12. Process for dyeing or printing a substrate, comprising contacting a dye composition as claimed in claim 3 with said substrate.

13. Substrate comprising a dye composition according to claim 1.

14. A printing paste, ink, or a dyeing bath for printing or dyeing a substrate comprising a dye composition as claimed in claim 3.

* * * * *